(12) United States Patent
Daghighian (10) Patent No.: US 6,602,488 B1
(45) Date of Patent: Aug. 5, 2003

(54) USE OF RADIOPHARMACEUTICALS AND INTRAOPERATIVE RADIATION PROBE FOR DELIVERY OF MEDICINAL TREATMENTS

(75) Inventor: Farhad Daghighian, Santa Monica, CA (US)

(73) Assignee: Intramedical Imaging, LLC, Los Angeles, CA (US)

( * ) Notice: Subject to any disclaimer, the term of this patent is extended or adjusted under 35 U.S.C. 154(b) by 0 days.

(21) Appl. No.: 09/518,457

(22) Filed: Mar. 3, 2000

(51) Int. Cl.$^7$ ............................................. A61K 5/055
(52) U.S. Cl. ..................... 424/9.3; 424/1.11; 424/9.1
(58) Field of Search ........................ 424/9.1, 9.3, 1.11, 424/9.4, 9.5, 9.6, 9.7

(56) References Cited

U.S. PATENT DOCUMENTS

| | | | |
|---|---|---|---|
| 3,112,402 A | 11/1963 | Okun et al. ................. 350/105 |
| 3,310,675 A | 3/1967 | Prickett et al. ............. 250/105 |
| 3,427,454 A | 2/1969 | Webb .......................... 250/83 |
| 3,598,109 A | 8/1971 | Kobayashi et al. ......... 128/2.05 |
| 3,609,370 A | 9/1971 | Peyser ....................... 250/105 |
| 3,628,021 A | 12/1971 | MacDonald ................ 250/105 |
| 3,670,719 A | 6/1972 | Kobayashi et al. ......... 128/2 A |
| 3,863,623 A | 2/1975 | Trueblood et al. .......... 128/2 A |
| 3,869,615 A | 3/1975 | Hoover et al. .............. 250/508 |
| 3,919,589 A | 11/1975 | Stevens ...................... 250/508 |
| 3,936,646 A | 2/1976 | Jonker ........................ 250/509 |
| 4,340,818 A | 7/1982 | Barnes ....................... 250/509 |
| 4,419,585 A | 12/1983 | Strauss et al. ............... 250/505 |
| 4,489,426 A | 12/1984 | Grass et al. ................ 378/150 |
| 4,502,147 A | 2/1985 | Michaels ................... 378/206 |
| 4,595,014 A | 6/1986 | Barrett et al. ............... 128/654 |
| 4,782,840 A | 11/1988 | Martin, Jr. et al. ......... 128/654 |
| 4,801,803 A | 1/1989 | Denen et al. ............... 250/336 |
| 4,932,412 A | 6/1990 | Goldenberg et al. ....... 128/654 |
| 4,959,547 A | 9/1990 | Carroll et al. .............. 250/336 |
| 4,976,266 A | 12/1990 | Huffman et al. ............ 128/549 |
| 4,995,396 A | 2/1991 | Inaba et al. ................. 128/654 |
| 5,008,546 A | 4/1991 | Mazziotta et al. .......... 250/366 |
| 5,014,708 A | 5/1991 | Hayashi et al. ............. 128/653 |
| 5,036,201 A | 7/1991 | Carroll et al. .............. 250/363 |
| 5,088,492 A | 2/1992 | Takayama et al. .......... 128/654 |
| 5,151,598 A | 9/1992 | Denen et al. ............... 250/336 |
| 5,170,055 A | 12/1992 | Carroll et al. .............. 250/336 |
| 5,275,166 A | 1/1994 | Vaitekunas et al. ......... 128/660 |
| 5,313,065 A | 5/1994 | Reed .......................... 250/368 |
| 5,325,855 A | 7/1994 | Daghighian et al. ........ 128/653 |

(List continued on next page.)

OTHER PUBLICATIONS

Barber et al, University of Arizona, *IEEE Transactions on Nuclear Science*, vol. ns–27, No. 1 Feb. 1980, *Small Radiation Detectors for Bronchoscopic Tumor Localization* pp. 496–502.

Woolfenden et al, *Lung Cancer Detection Using a Miniature Sodium Lodide Detector and Cobalt–57 Bleomycin*, Chest–85, 1, Jan., 1984, p. 84–88.

Primary Examiner—Dameron L. Jones
(74) Attorney, Agent, or Firm—Koppel, Jacobs, Patrick & Heybl; Michael J. Ram (57) ABSTRACT

A device for the delivery of genetic treatment material to radiopharmaceutical labeled diseased or malfunctioning candidate cells within a human body an a method for using the device. The method includes the labeling of target cells in a body with a radionuclide, the identification in situ of the candidate cells using a nuclear probe sensitive to the presence of the radionuclide label and delivery of the treatment compound to the cell while the probe is at the site of the labeled cells. More particularly, the invention relates to in situ gene therapy using a beta or gamma probe to locate labeled cells, also referred to as candidate cells, and the delivery of corrective genes to the candidate cells identified by the probe while the probe is positioned adjacent to the labeled and located cells.

6 Claims, 4 Drawing Sheets

U.S. PATENT DOCUMENTS

| | | | |
|---|---|---|---|
| 5,331,961 A | 7/1994 | Inaba et al. | 125/659 |
| 5,338,937 A | 8/1994 | Daghighian et al. | 250/368 |
| 5,383,456 A | 1/1995 | Arnold et al. | 128/653 |
| 5,424,546 A | 6/1995 | Okada et al. | 250/367 |
| 5,441,050 A | 8/1995 | Thurston et al. | 128/659 |
| 5,444,254 A | 8/1995 | Thomson | 250/370 |
| 5,471,988 A | 12/1995 | Fujio et al. | 128/660 |
| 5,485,846 A | 1/1996 | Webler et al. | 128/662 |
| 5,635,717 A | 6/1997 | Popescu | 250/368 |
| 5,657,759 A | 8/1997 | Essen-Moller | 128/654 |
| 5,682,888 A | 11/1997 | Olsen et al. | 128/653 |
| 5,703,056 A * | 12/1997 | Blasberg et al. | 514/44 |
| 5,776,064 A | 7/1998 | Kalfas et al. | 600/414 |
| 5,811,814 A | 9/1998 | Leone et al. | 250/368 |
| 5,814,295 A * | 9/1998 | Martin, Jr. et al. | 424/1.49 |
| 5,846,513 A * | 12/1998 | Carroll et al. | 424/1.11 |
| 5,857,463 A | 1/1999 | Thurston et al. | 128/659 |
| 5,899,860 A | 5/1999 | Pfeiffer et al. | 600/424 |
| 5,961,458 A | 10/1999 | Carroll et al. | 600/436 |

\* cited by examiner

_fig. 7_

_fig. 8_

_fig. 9_

USE OF RADIOPHARMACEUTICALS AND INTRAOPERATIVE RADIATION PROBE FOR DELIVERY OF MEDICINAL TREATMENTS

BACKGROUND OF THE INVENTION

The invention relates to the radiopharmaceutical labeling of diseased or malfunctioning candidate cells for subsequent treatment with a medicinal compound, the identification in situ of the candidate cells using a probe sensitive to the presence of the radiopharmaceutical label and then treatment of the identified cell. Addressed are improved instruments with enhanced operability, controllability, diagnostic capability and treatment capability. For example, the described devices can be used in an MRI environment, can provide a visual image as well as a radiation image, allow 3D imaging, and allow delivery of treatment compounds to the cell while the probe is at the site of the labeled cells. In one embodiment, the invention relates to in situ gene therapy using a beta or gamma probe to locate labeled cells, also referred to as candidate cells, and the delivery of corrective or therapeutic genes to the candidate cells identified by the probe while the probe is positioned adjacent to the labeled and located cells.

DESCRIPTION OF THE PRIOR ART

Most of the basic elements of biological materials have radiation emitting isotopes (e.g., C-11, N-13, O-15, F-18, I-124). For example, these compounds can be labeled with isotopes which emit positron, beta or gamma rays. More than 500 biochemicals have been labeled with these isotopes (e.g., amino acids, fatty acids, sugars antibodies, drugs, neuroreceptor ligands, nucleoside analogues, etc).

Recently, several chemical compounds have been labeled with various positron emitting tracer isotopes for the imaging of gene expression. For example I-124 labeled FIAU a 2'-fluoro-substituted nucleotide analogue, and PET studies performed on rats (Tjuvajev et al. Cancer Res 55, 6126–6132 (1995); Tjuvajev et al. Cancer Res 56, 4087–4095 (1996); Tjuvajev et al. Cancer Res. (1999) in Press) [8-$F^{18}$]-fluoroganciclovir has been used for PET studies of gene transduction in mice (Gambhir et al. J. Nucl. Med. (in Press) (1998); Haberkorn U et al. J Nucl. Med. 38: 1048–1054 (1997)). The goal of these procedures was to introduce radiolabeled tracers after gene therapy to determine if the gene therapy was successful. The presently described invention is fundamentally different because the below described invention entails radiolabeling of cells suitable for gene therapy and providing a gene therapy composition directly to labeled cells while targeted by the probe.

In attempts to locate cancerous cells numerous labeling techniques have been developed to identify the site of those cancerous cells. It was recognized many years ago that fibrin, while not a tumor specific antigen, was known to be more prevalent in the vicinity of tumors due to the inflammatory process accompanying the cell proliferation. Therefore radiolabeled immunoglobulin was used for tumor localization (Day, E. O.; Planisek, J. A.; Pressman D.; "Localization of Radioiodinated Rat Fibrinogen in Transplanted Rat Tumors", *J. Natl. Cancer Inst.* 23: 799–812, 1959. Sparr, J. L.; Bale, W. F.; Marrock, D. D.; Dewey, W. O.; McCardle, R. J.; Harper, P. V.; "Labeled Antibodies to Human Fibrinogen. Diagnostic Studies and Therapeutic Trails", *Cancer*, 20: 865–870, 1967.) In all these works the goal was to use radiolabled tracers after gene therapy to determine if the gene therapy was successful. The new method described in this patent application is fundamentally different because radio labeled tracers are used to locate the cells that are suitable candidates for gene therapy before the therapy is applied.

More specific labeling was accomplished by Goldbenberg, et al. by the use of $I^{131}$-labelled heterologous (goat) antibodies to human carcinoembryonic antigen (CEA). (Goldenberg, D. M.: "Oncofetal and other Tumor-associated Antigens of the Human Digestive System", *Curr. Top. Pathol.* 63: 289–342, 1976. Goldenberg, D. M.; Deland, F.; Kim, E. E.: "Human Chorionic Gonadotrophin Radio-antibodies in the Radio immunodetection of Cancer and the Disclosure of Occult Metastases" *Proc. Nat'l. Acad. Sci.* 78: 7754–7758, 1981.; Goldenberg, D. M.; Deland, F.; Kim, E. E., et al.: "Use of Radio labeled Antibodies to Carcinoembryonic Antigen for the Detection and Localization of Diverse Cancers by External Photoscanning", *N. Engl. J. Med.* 298: 1384–1388, 1978.; Goldenberg, D. M.; Preston, D. F.; Primus, F. J.; Hansen, H. J.: "Photoscan Localization of GW-39 Tumors in Hamsters Using Radiolabeled Anti-carcinoembryonic Antigen Immunoglobulin" *J. Cancer Res.* 34: 1–9, 1974.; Goldenberg, D. M.; Sharkey, R. M.; Primus, F. J.: "Carcinoembryonic Antigen in Histopathology: Immunoperoxidase Staining of Conventional Tissue Sections", *J. Natl. Cancer Inst.* 57: 11–22, 1976.) CEA is a tumor-associated antigen of gastrointestinal cancer, particularly colon and pancreatic cancer, first described by Gold. (Gold, P., Freedman, S. O.: "Demonstration of Tumor Specific Antigen in Human Colonic Carcinomata by Immunologic Tolerance and Absorption Techniques", *J. Exp. Med.* 121: 439–462, 1965.) Other labeled antibodies usable for tagging tumor cells include monoclonal antibody 17-1A and its F(ab')$_2$ fragment (Wistar Institute, Philadelphia, Pa.), mono-clonal antibody 19-9 and its F(ab')$_2$ fragment (Centocor, Inc., Philadelphia, Pa.), monoclonal antibody B72.3 (Dr. Jeffrey Schlom, National Cancer Institute) and CC49 and CC83, both second generation B72.3 antibodies. These are identified as examples of suitable materials and are not meant to limit the scope of compounds usable to label cells. Many other compounds, such as single chained antibodies (SCAs) disclosed in U.S. Pat. No. 4,946,778, capable of labeling specific cells, are identified in the literature and are constantly being discovered and/or developed. Labeling nucleotides detectable by a gamma probe include technetium $Tc^{99}$, iodine $I^{123}$, $I^{125}$, and $I^{131}$, indium $In^{111}$, selenium $Se^{75}$, and cobalt $Co^{57}$. These and other radioisotopes can be detected by beta or gamma probes.

Martin et al., U.S. Pat. No. 4,782,840, incorporated herein by reference, describes a procedure which requires the administration of $I^{125}$ labeled antibody or antibody fragments to a patient to label cancerous tissue. Some time after administration (2 to 21 days) the suspected site is accessed surgically and, using a hand-held gamma probe, the labeled tissue is located and surgically removed.

Applicant is a co-inventor on U.S. Pat. Nos. 5,008,546, 5,325,855 and 5,338,937, which describe and claim variations to prior know intraoperative radiation probes. Others describe the use of gamma probes as a biopsy probe for locating, localizing or mapping tagged tissue located throughout the body and particularly near the liver, kidney, or blood vessels or to localize lymph nodes (U.S. Pat. Nos. 4,959,547, 5,170,055 and 5,036,201 to Carroll et al; U.S. Pat. No. 5,383,456 to Arnold et al.). Leone et al, U.S. Pat. No. 5,811,814 describes a catheter, including fiber optics and a scintillation crystal, suitable for locating concentrations of alpha, beta, gamma or X-ray labeled compounds introduced into the arteries and veins.

The use of radiation detection probes placed through scopes to locate radionuclide labeled tissue has been described in the literature for many years. Both Barber et al and Woolfenden et al. described the insertion of a gamma ray detection probe through an open channel in a bronco-scope. (Barber, H. B., Woolfenden, J. M., Donahue, D. J., Nevin, W. S., "Small Radiation Detectors for Bronchoscopic Tumor Localization", *IEEE Transactions on Nuclear Science*, NS-27, No. 1 Febuary 1980; Woolfenden, J. M., Nevin, W. S., Barber, H. B., Donahue, D. J., "Lung Cancer Detection Using a Miniature Sodium Iodide Detector and Cobalt-57 Bleomycin", *Chest*, 85, 1, January 1984). Goldenberg, U.S. Pat. No. 4, 932,412, issued Jun. 12, 1990 claimed the same technique, namely the use of a radiation detection probe placed through an endoscope to locate radionuclide labeled tissue.

U.S. Pat. No. 5,846,513 to Carroll et al. describes a probe for percutaneous insertion into a body through a delivery sheath followed by the removal of the probe and insertion through the same sheath of an instrument, such as a resectoscope, to remove the identified tissue. Alternatively, the '513 patent discloses that, following removal of the probe, other tumor destroying techniques can be practiced by delivering a treatment media or device through the sheath, such as cancer cell necrotizing agents, high intensity ultrasound, microwave energy, laser energy, heat electrocoagulation, or the introduction of tumor destructive chemical agents such as free radical promoters, copper or iron ions, oxidants, iodine, tissue digestive enzymes, alcohol or radioactive seeds. However, Carroll et al did not suggest the delivery of compositions for gene therapy which, as discussed below, function in a fundamentally different manner from chemical, mechanical or electrical tumor destruction techniques.

U.S. Pat. No. 5,014,708 discloses a device insertable within the body which includes in combination, a radiation sensing probe with an ultrasonic tip and aspiration function to remove tissue released by the vibrating ultrasound tip. U.S. Pat. No. 4,995,396 sets forth an endoscope which includes, in combination, a radiation detecting probe with means to deliver tumor affinable chemicals which can then be activated by laser light transmitted through fiber optics also enclosed within the endoscope. Neither patent suggests gene therapy or the other new functions described below.

Another technique attempted to treat cancer is adoptive immunotherapy. Using lymphokines such as Interlukin-2 (IL-2) and lymphokine-activated killer cells (LAK) derived from patient peripheral blood, patients with melanoma and renal cell cancer have shown a significant positive response. A related approach is the in-vitro placement of cytokine genes into tumor specific lymphocytes. After a few days the cytokine gene supplemented lymphocytes are delivered locally to a tumor.

Rosenberg, et al. demonstrated that a small but significant percentage of patients with melanoma and renal cell cancer could achieve a long-lasting response. (Rosenberg, et al., "Adoptive Cellular Therapy: Clinical Applications", *Biologic Therapy of Cancer*, De Vita, et al. (Eds.), J. B. Lippincott Company, Philadelphia, Pa., 1991.) A second approach to adoptive immunotherapy is to expand lymphocytes from tumors in culture. (Rosenberg, et al., "Adoptive Cellular Therapy: Clinical Applications", *Biologic Therapy of Cancer*, De Vita, et al. (Eds.), J. B. Lippincott Company, Philadelphia, Pa., (1991); Topalian, et al. "Tumor Infiltrating Lymphocytes: Evidence of Specific Immune Reactions Against Growing Cancers in Mice and Human", *Important Advances in Oncology* 1990, De Vita, et al. (Eds.), J.B. Lippincott Company, Philadelphia, Pa., p. 19 (1990), and Rosenberg, et al., "Use of Tumor-Infiltrating Lymphocytes and Interleukin-2 in the Immunotherapy of Patients with Metastatic Melanoma", *N. Engl. J. Med.*, 25: 1671, 1988.) Using these tumor-infiltrating lymphocytes (TIL), several research groups have documented superior tumor cytolytic activity and better delivery of these TIL cells to tumors than LAK cells. (Rosenberg, et al., *N. Engl. J. Med.*, id.; Diliman, et al., "Continuous Interleukin-2 and Tumor-Infiltrating Lymphocytes as Treatment of Advanced Melanoma", *Cancer*, 68: 1, 1991; Kradin, et al., "Tumor-Infiltrating Lymphocytes in Interleukin-2 in Treatment of Advanced Cancer", *Lancet*, 33: 577, 1989; and Bukowski, et al., "Clinical Results and Characterization of Tumor-Infiltrating Lymphocytes with or without Recombinant Interleukin-2 in Human Metastatic Renal Cell Carcinoma", *Cancer Res.* 51: 4199, 1991.) In general, TIL Cells appear to be therapeutically effective for patients with melanoma. Tumor-infiltrating lymphocytes have been generated from many solid tumors, including colon and breast cancer; however, these cells do not appear to mediate tumor-specific cytolytic activity in vitro and it is not known if these cells will be effective in adoptive immunotherapy models. (Rosenberg, "Gene Therapy of Cancer", *Important Advances in Oncology*, 1992, De Vita, et al. (EDS.), J.B. Lippincott Co., New York, N.Y., pp 17–18, 1992.)

Another approach to tumor therapy with tumor-specific lymphocytes is the placement of cytokine genes in cells which can deliver cytokines locally to the tumor. (Kasid, et al., "Human Gene Transfer: Characterization of Human Tumor Infiltrating Lymphocytes as Vehicles for Retroviral-Mediated Gene Transfer in Man", *Proc. Natl. Acad. Sci. USA*, 87: 473–477, 1990; and Rosenberg, et al., "Gene Transfer into Humans: Immunotherapy of Patients with Advanced Melanoma Using Tumor Infiltrating Lymphocytes Modified by Retroviral Gene Transduction", *New Engl. J. Med.*, 323: 570–578, 1990.) It has been shown in several model systems that tumor cells transfected with various cytokine genes including IL-2, gamma interferon, and tumor necrosis factor (TNF), are more immunogenic and less tumorigenic than parent cells that do not produce cytokines. (Gansbacher, et al., "Retroviral Vector-Mediated Gamma Interferon Gene Transfer into Tumor Cells Generates Potent and Long Lasting Antitumor Immunity", *Cancer Res.* 50: 7820–7825, 1990; Gansbacher, et al., "Interleukin2 Gene Transfer into Tumor Cells Abrogates Tumorigenecity and Induces Protective Immunity", *J. Exp. Med.*, 172: 1217–1224, 1990; and Blankenstein, et al., "Tumor Suppression after Tumor Cell-Targeted Tumor Necrosis Factor-Alpha Gene Transfer", *J.,Exp. Med.* 173: 1047–1052, 1991.)

It appears that local production of cytokines near tumor cells can inhibit tumor growth and stimulate an immune response. It would therefore appear useful to find lymphocytes that recognize tumors and are capable of secreting various cytokines in response to tumors and to deliver these lymphocytes to labeled tumor cells for adoptive immunotherapy. It has been shown that certain TIL cells that secrete gamma-interferon and TNF-alpha will cause tumor regression in vivo, even though they do not display direct tumor cytotoxicity in vitro. (Barth, et al., "Interferon-Gamma and Tumor Necrosis Factor Have a Role in Tumor Regression Mediated by Murine. $CD_8+$ Tumor-Infiltrating Lymphocytes", *J. Exp. Med.*, 173: 647, 1991.)

An alternative source of tumor lymphocytes is lymph nodes. Martin et al., U.S. Pat. No. 5,814,295, describes a method of locating, within cancer patients, lymph nodes enriched in tumor reactive lymphocytes so these cells can be harvested, cultured and delivered to the donor patient. The method comprises administering to the patient a radiolabeled locator (such as an antibody) which, in addition to concentration in cancer tissue, also concentrates in the lymph nodes, which are rich in tumor reactive lymphocytes. A gamma probe is then used to locate lymph nodes with increased radiation levels and those nodes are surgically excised. Nodes that appear normal (i.e. free of gross metastatic disease) but which took up the radiolabeled antibody are separated and cultured to proliferate tumor reactive cells with tumor-specific T lymphocytes therein. The cultured tumor reactive cells can then undergo gene therapy in-vitro as described above and, following a several day incubation period, transfused into the patient in accordance with adoptive immunotherapy regimes. This is fundamentally different from the invention described herein where the tumor reactive cells are delivered in vivo to the tumor and allowed to attack the tumor cell within the body of the cancer patient.

Gene therapy involves the insertion of genes or parts of DNA into cells or the cell membrane such that they become part of the genetic structure of the cell. Typically, a DNA vector capable of expressing a suitable gene product in the cells of the target organism is transferred into the cells of the organism, through one of a variety of processes so that it interacts with the genetic material of the cell. Prior art mechanisms for the insertion of genetic material into living tissues include direct microinjection, electroporation, (a technique in which individual cells are subjected to an electric shock to cause those cells to uptake DNA from a surrounding fluid), liposome-mediated transformation, (DNA or other genetic material is encapsulated in bilipid vesicles which have an affinity to the cell walls of target organisms), and the use of specific types of biological vectors or carriers which have the ability to transfect genetic material carried within them into specific target organisms. For example, Nemunaitis et al reports on the beneficial effects of the direct injection into tumors in the lung of Adp 53 in combination with cisplatin (Nemunaitis, J, et al "Adenovirus-Mediated p53 Gene Transfer in sequence with Cisplatin to Tumors of Patients with Non-Small-Cell Lung Tumor," *J.Clin. Oncology*, 18, No 3, (Febuary, 2000) p609–622.

One general technique applicable to a large range of hosts is referred to as particle mediated genetic transformation. In this technique, the genetic material, (RNA or DNA) is coated onto small carrier particles. The particles are then accelerated toward target cells where the particles impact the cells and penetrate the cell walls, carrying the genetic material into the cells. At least a proportion of the cells into which the genetic material is delivered express the inserted genetic material and another smaller proportion of the cells may integrate the delivered genetic material into the cells native genetic material.

One method of accelerating coated carrier particles utilizes a larger carrier object, sometimes referred to as a macroprojectile. The carrier particles are positioned inside the macroprojectile. The macroprojectile is then accelerated at a high speed toward a stopping plate. One means of accelerating the microprojectile is to use a gunpowder driven device in which the hot gases generated by a gunpowder discharge form a hot gas shock wave, which accelerates the macroprojectile. When the macroprojectile strikes a stopping plate with a hole therein, the microprojectiles continue their travel through the hole and eventually strike the target cells. This and other acceleration techniques have been described in U.S. Pat. No. 4,945,050 issued to Sanford et al. and entitled "Method For Transporting Substances Into Living Cells And Tissues And Apparatus Therefore" incorporated by reference herein.

A second technique developed for the acceleration of carrier particles is based on a shock wave created by a high voltage electric spark discharge. This technique involves an apparatus having a pair of spaced electrodes placed in a spark discharge chamber. The high voltage discharge is then passed between the electrodes to vaporize a droplet of water placed between the electrodes. The spark discharge vaporizes the water droplet creating a pressure wave, which accelerates a carrier material previously placed in the discharge chamber. The carrier transports the particles which are coated with the genetic materials to be delivered. The carrier is accelerated toward a retainer, where it is stopped, the particles are separated from the carrier, and the particles carried thereby pass on into the biological tissues.

This second technique has been incorporated into a handheld device that can be use for accelerating particles carrying biological materials into large whole organisms. The hand held device is described in U.S. Pat. No. 5,149,655 to an "Apparatus For Genetic Transformation". issued to McCabe et al.

A variation on the second technique for acceleration of carrier particles is based on an expanding gas shock wave, and a planar surface having carrier particles positioned on the target side of the planar surface. The shock wave that actually impacts the target area is substantially reduced when this technique is utilized. In addition, the apparatus used with this technique does not subject target cells to radiant heat or appreciable acoustic energy. Hence cell differentiation and successful cell transformation is maximized. This technique is described in U.S. Pat. No. 5,204,253, entitled "Method and Apparatus For Introducing Biological Substances Into Living Cells." which issued to Sanford et al.

In this third technique, the delivery instrument incorporates a high pressure gas delivery system, a mechanism to generate an instantaneous gas shock out of the high pressure system, an enclosure into which the gas shock is released, contained and vented and a throat region which translates the gas shock into a particle acceleration force. The expanding gas shock is directed at, and impacts on, a back surface of the planar insertion mechanism (the carrier particles being on the front surface of the insertion mechanism). The particles are then disbursed from the front surface over a wide region of the target cells.

All of the techniques discussed can generate only a single potentially traumatic, essentially instantaneous burst of carrier particles and thus are single shot insertion devices. In order to utilize the single shot apparatus a second time, a new carrier with genetic material thereon must be inserted into the device.

U.S. Pat. No. 5,525,510 is directed to an apparatus for injecting a continuous stream of carrier particles carrying genetic material into living cells. It includes a body member having an acceleration channel along a central axis, with the channel having an outlet at an exit end. The body also includes a source chamber connected to a compressed gas source and to the channel. Particles are placed on a carrier mounted in the body member in a position exposed to the channel so that a gas stream flowing in the channel can pick up carrier particles off of the particle carrier. A gas stream diverter is placed on the body adjacent the outlet of the channel diverts the gas stream away from the direction of flight of the carrier particles as they exit the body. In this manner a continuous stream of particles carrying genetic material can be directed to the target cells.

It has been discovered that cancer cells may have a defective gene structure. It is believed that correction of this gene structure, or modification of that structure can convert the cancerous cell to a normal cell or, as a minimum, modify or retard the cancerous characteristics of those cells and prevent the proliferation of the cancer cells. Alternatively, cancer cells can be transfected by DNA that makes them undergo the apoptosis process. Gene therapy is not limited to cancer cells as it is believed that a gene defect can be identified in other abnormal cells. Also, genes can be delivered to the cell to cause the cell to then generate therapeutic substances. The inventive devices described herein can localize the schemic tissues and allow the effective and accurate insertion of therapeutic genes. There are several radiolableled compounds that can be accumulated in schemic tissue. For example, cells undergoing the apoptotic process can be targeted. Additionally, genes can be inserted in myocardial cells causing them to generate angiogenic factor, which promote the generation of blood vessels.

It has also been recognized that diseased cells or tissue can be radiolabeled using various cell specific, tagged compounds. It is also known that these labeled cells or labeled tissue can be located using a probe containing a radiation sensitive detector mounted to receive emissions from the radiolabeled tissue. However, no one has provided a readily usable means for delivering, in vivo, corrective genes directly to the labeled (candidate) tissue in the patient's body while that tissue is under surveillance by the probe.

SUMMARY OF THE INVENTION

The invention comprises a probe for the in vivo location of radiolabeled cells or tissue using a radiation sensitive crystal or other detector devices, such as semiconductor detector materials, mounted in the tip of a tubular device insertable into a mammalian body to the region of the suspected radiolabeled cells. As used herein, each reference to "radiolabeled cells" alternatively is a reference to radiolabeled tissue or tissue containing radiolabeled cells. The device includes channels therein, or associated therewith, for placement of compositions for modifying, in a desired manner, the radiolabeled cells directly on or in the labeled cells, or in the immediate vicinity of the labeled cells, while the probe is targeting the labeled cells. The invention also includes a method for gene therapy comprising marking abnormal cells or abnormal tissues with a radioactive tag, targeting those tagged cells using a probe directionally sensitive to the proximity of radionuclides and, through a channel placed at the site of the target cells along with the probe, delivering genetic material prepared for gene therapy treatment purposes.

The invention also contemplates the use of a collimating material unaffected by, or not inferring with, a magnetic field, such as a gold collimator, so the probe can be used intraoperatively within the field of an MRI diagnostic instrument.

Further, devices within the scope of the invention can include fiber optic channels, which will allow illumination and/or optical visualization of the targeted tissue at the same time a radiation image is being generated. More then one fiber optic channel will allow a 3D image to be generated.

Still further, devices within the scope of the invention can also include position-locating means attached to the distal end of the detector. This allows the location of the detector tip within the patient's body to be continuously monitored and recorded and, simultaneously, a visual image of targeted tissue recorded with a radiation count from the labeled tissue superimposed digitally thereon. This will provide a contemporaneous viewable image of the labeled tumor, an audible indication of radiation intensity across the targeted site, and a digital visual record of the procedure.

It should be recognized that each of these concepts, namely a) the delivery of gene therapy b) use of the probe in an MRI field c) mapping of the operative site, and d) the generation of an optical and radiation image may be utilized independently or two or more of these concepts may be combined in a single device.

DESCRIPTION OF THE FIGURES

FIG. 1 is cutaway side view of a first embodiment of a probe incorporating features of the invention having a central flow lumen.

FIG. 2 is cross sectional view of the first embodiment of the probe taken along line 2—2 of FIG. 1.

FIG. 3 is cross sectional view of the first embodiment of the probe taken along line 3—3 of FIG. 1.

FIG. 4 is cutaway side view of a second embodiment of a probe incorporating features of the invention having flow lumens in the wall of the probe.

FIG. 5 is cross sectional view of the second embodiment of the probe taken long line 5—5 of FIG. 4.

FIG. 6 is cross sectional view of the second embodiment of the probe taken along line 6—6 of FIG. 4.

FIG. 7 is cutaway side view of a third embodiment of a probe incorporating features of the invention acting in cooperation with a separate delivery catheter.

FIG. 8 is a schematic drawing showing a probe incorporating features of the invention attached to radiation indicating instrumentation and a source of genetic material for treatment purposes.

FIG. 9 is a cutaway view of a distal tip of a fourth embodiment which allows sideways viewing of radionuclide labeled cells and delivery of treatment material to those targeted cells.

FIG. 10 is a variation of FIG. 4 incorporating a preamplifier in the catheter tip and signal transmitter for locating the position of the tip.

DETAILED DESCRIPTION OF THE INVENTION

The invention comprises a body insertable probe for in vivo location of radiolabeled tissue, the probe including means for delivery of cell altering genes directly to, or to the immediate vicinity of, the labeled cells. The means for delivery of the gene therapy composition may include a conduit for delivery of a liquid containing the genetic material being delivered or other delivery means known to those of ordinary skill in the art including, but not limited to, electroportation, liposomal formulations, microinjection, or the use of a gene gun or other gene delivery devices. This will allow corrective genetic material (i.e. gene therapy) to be delivered directly to the target cells. Because the device allows direct, rather than systemic, delivery of the genetic material to the targeted cells, the concentration of the materials delivered can be increased and compounds which might negatively effect other body organs or normal tissue can be delivered with greatly reduced risk of systemic damage. A method of using the probe with gene therapy delivery means is also included.

In a preferred embodiment the body insertable probe comprises a hollow tube, such as an endoscope or catheter, with a radiation detector mounted at the distal end thereof. The probe includes at least one lumen from its proximal to distal end for the delivery of the genetic material to the labeled tissue located by the probe. The detector can be various different materials. For example, suitable semiconductor detectors such as silicon, ion implanted silicon, cadmium telluride, or zinc cadmium telluride or scintillation crystals such as sodium iodide, mercury iodide, bismuth germanate oxide, leutitium ortho oxysilicate or, in the alternative a scintillation fluid (BC-505 or BC-519 from Bicron Corp., Newburg, Ohio) can be used. Photons generated by scintillation within the crystal can be locally detected by, for example a photodiode, or transmitted through a bundle of optical fibers to a remotely located photo multiplier tube and then radiation at the tissue source measured and/or positionally located. The detector is located in the tip of a diagnostic catheter arranged to look forward or sidewardly by the addition of a collimating sleeve. The detector can also be designed with a hole through its center, the axis thereof being the same as an axis through the lumen down the center of the catheter. The catheter tip can be designed to articulate or bend so it can be manipulate through turns in body vessels or bent to point the crystal toward particular target tissue within the body by using a guide wire through a central lumen or a lumen in the wall of the catheter. The invention also contemplates the use of a separate gene delivery device introduced into the patient's body and maneuvered to the same target site along with the probe so that it can be separately manipulated to deliver the genetic treatment material to the probe-located target cells.

Figures 1, 2, 3:
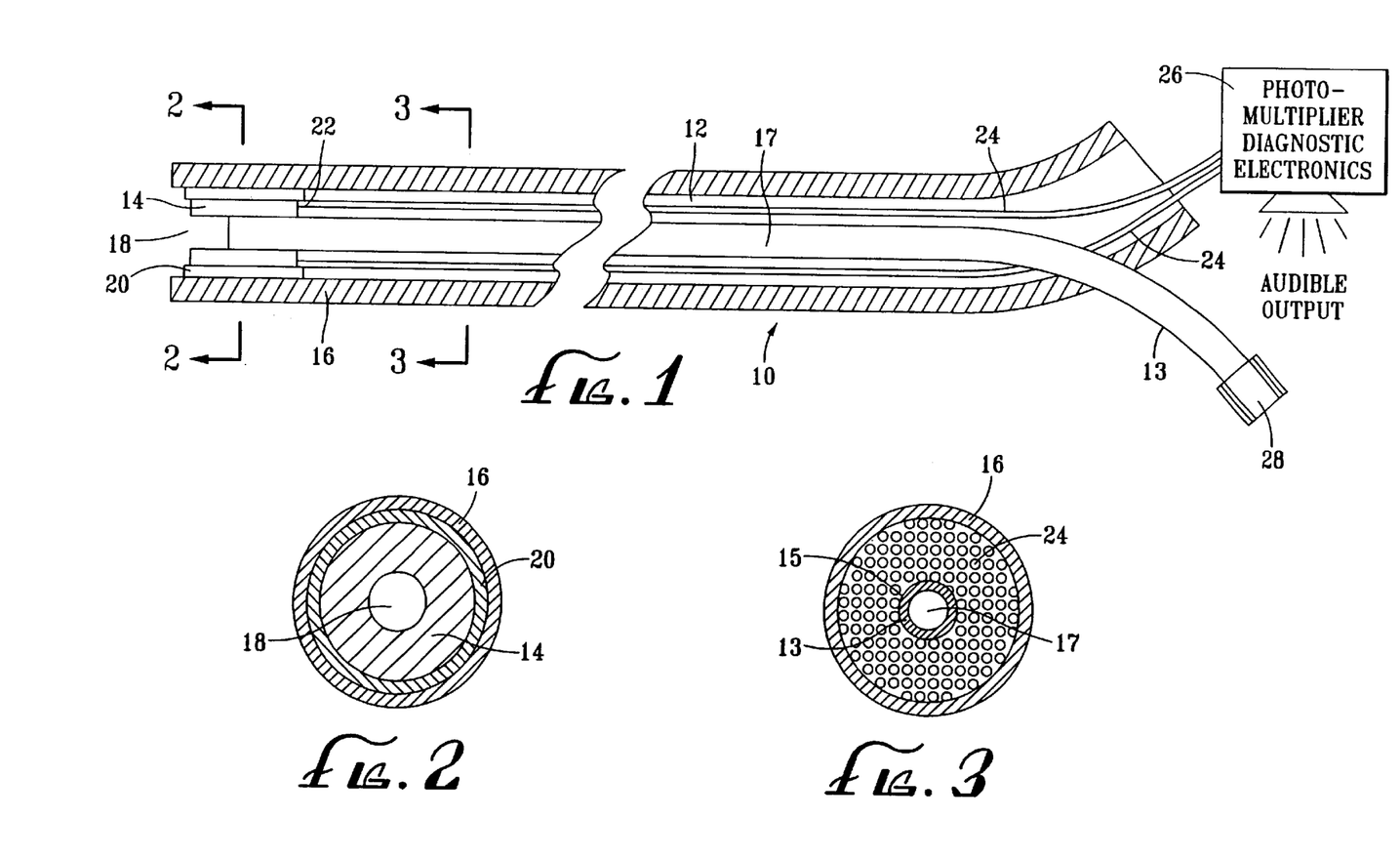

FIGS. 1–3 show a first embodiment of the probe 10 incorporating a lumen 12 for delivery of the genetic material to target cells. The detector or scintillation crystal 14, located within the distal end of the lumen 12 of the tube 16, has an axial bore 18 longitudinally therethrough. Within the lumen 12 is a delivery tube 13 with its wall 15 attached at one end to the scintillation crystal 14 so the lumen 17 in the delivery tube 13 is contiguous with the bore 18. On the proximal end of the delivery tube 13 is a connector 28, such as those typically used on catheters or feed tubes on medical devices, for attaching to a source of a cell-altering genetic material. A liquid containing cell-altering genetic material or genetic material delivered by way of a gene gun or other gene delivery mechanism fed through the delivery tube 13 and the bore 18 can be dispensed through the lumen 12 onto target cells directly distal to the crystal. When the scintillation crystal is used for detecting beta-ray emissions from a labeled target the portion of the tube 16 surrounding the crystal may be adequate to shield and collimate the emissions. As a result emissions primarily distal to the probe will be sensed. However, when the target cells are labeled with radionuclides emitting gamma particles, which have a greater penetration capability, the detector or scintillation crystal must be surrounded by a collimating shield 20 so that only gamma particles emanating from a selected direction (in the case of FIG. 1, directly distal to the crystal) are seen by the crystal. The shield may be fixed in position or, as suggested by the prior art, movable longitudlinally by a wire or pneumatics to widen or shorten the viewing window and, as a result, vary the angle of detection.

Magnetic Resonance Imaging (MRI) is a powerful anatomical imaging modality used for in vivo localization of tumors and other abnormalities in humans. While a probe or small imaging cameras can be used to locate tissue with a higher uptake of a radioactive tracer localized in vivo, these two procedures can not be used at the same time (concurrently). The problem is the interference of the MRI magnetic field with the photomultiplier tube connected to the radiation probe or the interference by paramagnetic/ferromagnetic materials used in the radiation probe, disrupting the MRI image. Lead as well as the other metals, which can disturb a magnetic field, are commonly used as collimating shields in the probes. It has been found that using nonmagnetic materials, such as gold, has distinct advantages. The gold collimator will allow the probe to be used within the field of a MRI diagnostic scanner. By combining a radiation probe investigation and MR imaging concurrently, a new complementary mechanism of identifying abnormal tissues can be realized. For example, the nuclear radiation probe investigation can be done intraluminally (intracavity), laprascopically, or other forms of minimally invasive or open surgeries can be performed. Thus, surgeons can simultaneously locate tumors by MRI, and, when labeled, target cancerous tissue with the probe and treat the tissue, all being performed within a MRI unit surrounding the surgical site and without interfering with the MRI image generated.

Attached, in an optically transmitting manner, to the proximal end 22 of the crystal are optical fibers 24 which transmit photons generated by scintillation within the crystal to the proximal end of the probe 10 where they can be detected and counted by a photomultiplier assembly and electronic diagnostics. Use of long optical fibers 24 also allows location of the photomultiplier tube outside of, and a safe distance from interference by, the magnetic field. Flexible gamma and beta probes within the scope of the invention use a scintillator or radiation detector coupled to a distant photomultiplier tube via a long (5 to 10 foot) fiber optic light guide. All of the materials used at the tip of these probes and along the fiber optic cable are non-magnetic. For example, the collimator is made from pure gold and there is no substance in the jacket of the cable that would interfere with the MRI.

In a preferred embodiment, scintillation in the crystal 14, caused by a radionuclide emitting labeled cells directly distal to the tip of the probe 10, is detected by photomultiplier diagnostic electronics 26 and an audible sound or click is generated for each detected photon or defined packet of multiple photons. The sounds or clicks are generally emitted at least every 0.1 sec such that targets with higher radio activity cause a more persistent and constant clicking. The diagnostic electronics 26 may also include computer storage capability so that a record of the probe scan can be reviewed. The storage of radiation emission levels has added value when the probe contains position sensing means as described below and shown in FIG. 10, and/or optical image generating means, which allows mapping to create an optical and radiation image of the labeled tissue. In other words, an image is generated which shows the location of the probe tip within the body along with radiation counts at that position. This image and radiation concentration can be further enhanced by providing fiber optics in the wall of the probe, which allows illumination of the tissue being probed. Another imaging-grade optical fiber bundle can be used to generate a photographic or digital image of that tissue. Using digital image manipulation techniques, the radiation counted can be imposed on the visual image.

Figure 4:
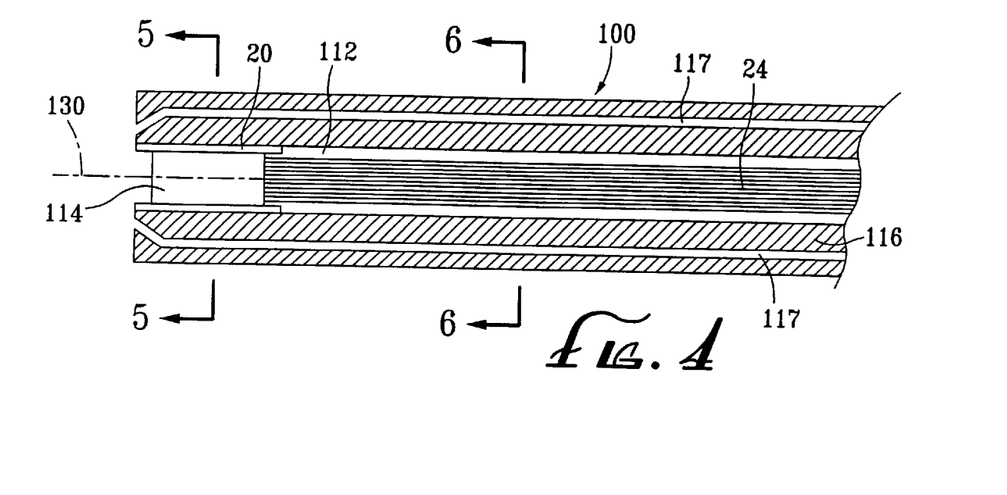
Figure 5:
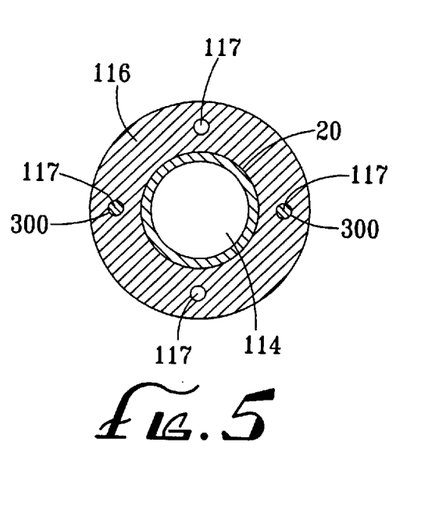
Figure 6:
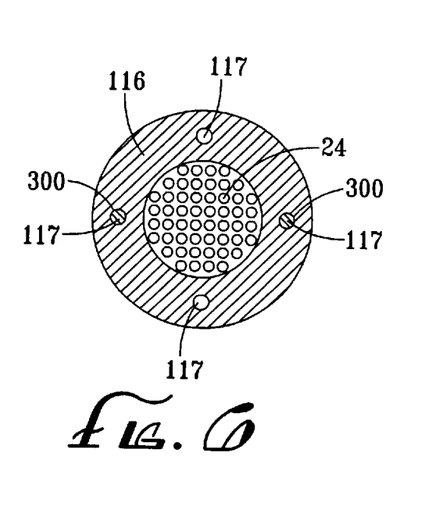

FIGS. 4–6 show a second embodiment of the probe 100, which utilizes a solid (no central bore) scintillation crystal 114. In a manner similar to the first embodiment, the cylindrical surfaces of the crystal 100 may be covered by a shield 20. Optical fibers 24 extending proximally therefrom through a central lumen 112 are attached to diagnostic electronics 26 (not shown). This embodiment includes one or more lumens 117 within the wall of the tube 116. These lumens 117 can be used for the placement of a guide wire or steering wires typically used for placing and guiding catheters or endoscopes to a desired location. Also, one or more of these lumens may have optically fiber bundles therein for delivering illuminating light to the target site and/or obtaining a visual image of the target tissue. Alternatively, the lumens provide a channel for delivering a gene therapy composition to tagged tissue located by the crystal at the distal end of the probe. As shown in FIG. 4, the lumens used to deliver the genetic material may be aimed, at the distal end of the device, to direct the delivered material to a point, i.e., a target 130, along the central axis of the crystal and a fixed distance from the distal tip of the probe. Also, while only 4 lumens are shown in the catheter wall, one skilled in the art will recognize that additional lumens may be utilized. FIGS. 5 and 6 show two lumens 117 for delivery of genetic treatment materials and two lumens 117 with an optical fiber 300 or bundle of fibers therein.

Figure 7:
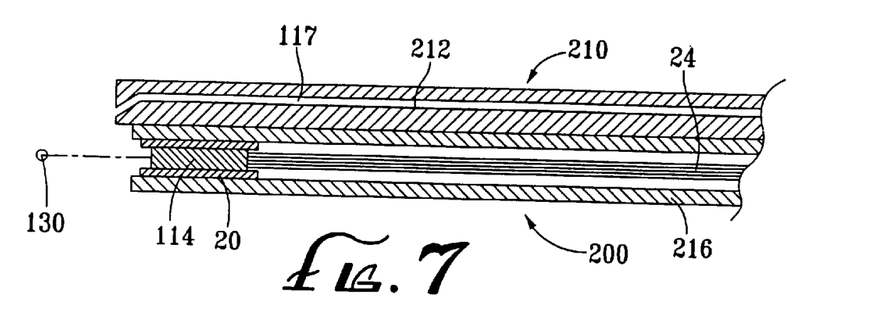
Figure 8:
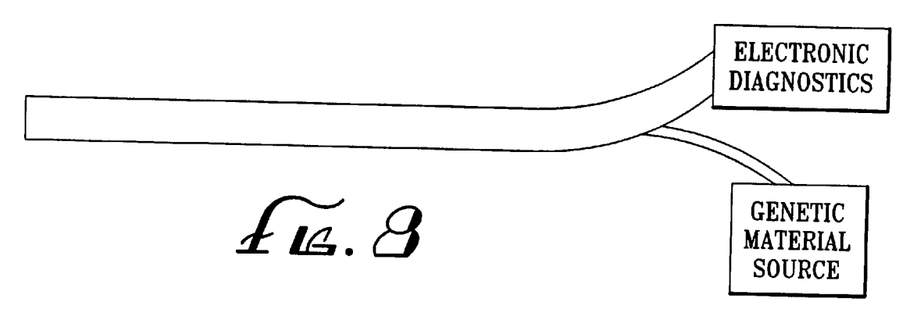
Figure 9:
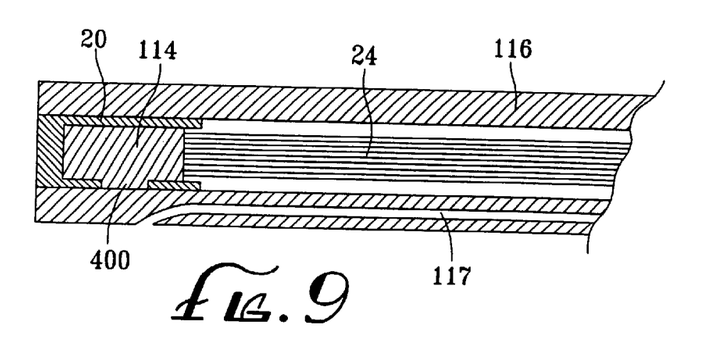

FIG. 7 shows a probe 200 with the scintillation crystal 114 and fiber optics 24 in its own delivery tube 216. The gene therapy delivery catheter 210 is a separate tube with a central lumen 212. While the delivery catheter 210 is shown attached to the probe 200 to provide deliver of the gene therapy to the targeted tissue 130, one skilled in the art will recognize that the delivery catheter 210 may be placed within the body at the operative site and guided separately from the probe 200 as long as it is specifically directed to the tagged tissue located by the probe 200. FIG. 9 is a still further embodiment which includes a side viewing scintillation crystal 114 which incorporates a shield 20 with a side opening 400 and a delivery channel 117 position to deliver the genetic treatment to the labeled and located tissue.

While each of the embodiments show a channel for delivery of a treatment material to the target cell it is contemplated that this conduit generally represents a channel for treatment delivering and can also be used for delivery of genetic treatment material in accordance with various prior art techniques such as discussed above, often referred to as a gene gun, for propelling a gene coated particle into a cell.

Figure 10:
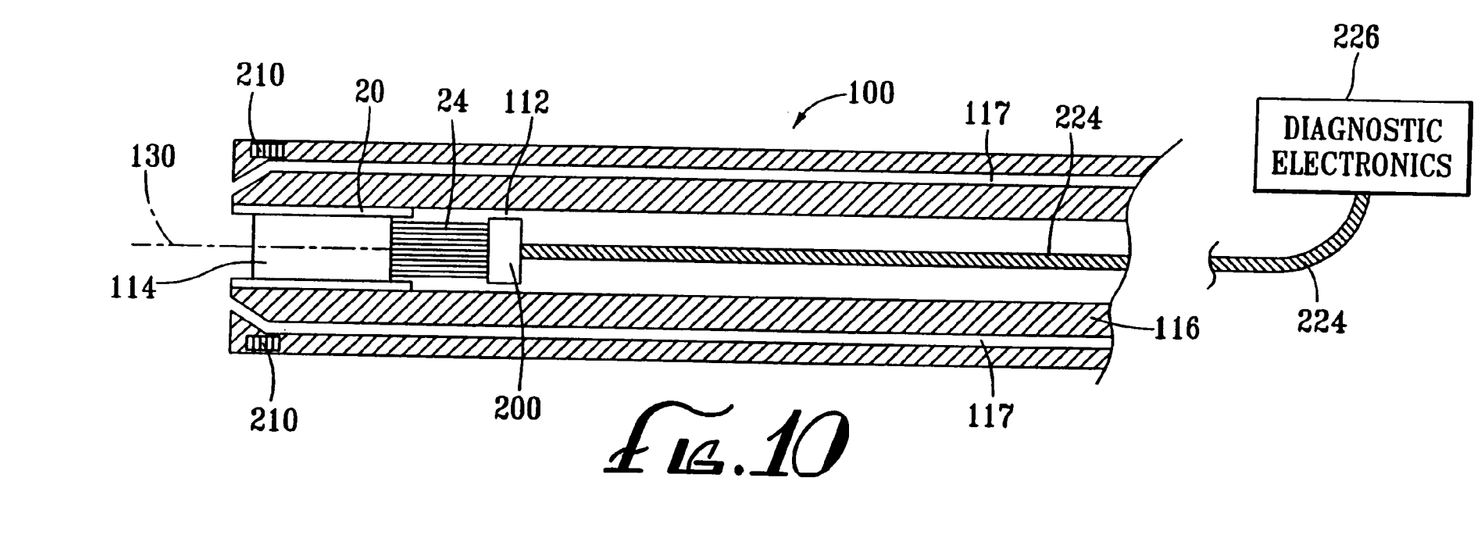

FIG. 10 shows a further embodiment with a shielded detector 114 in the tip of the probe connected by fiber optics 24 to a preamplifier 200, also mounted near the distal end of the probe 100. The preamplifier is then connected electrically or optical through cable 224 to diagnostic electronics 226 mounted in a location convenient to the sight and hearing of device operator.

FIG. 10 also shows position locating transmitters 210 in the wall of the distal end of the probe 100. These transmitters can, of course, be added to any of the other embodiments or replaced by detectable inserts in the distal tip. Alternatively, mechanical electrical or optical means on the proximal end of the probe can also be used to locate and track the probe tip.

To use any of the embodiments disclosed herein, or any variations thereof that one skilled in the art, based on the teaching herein, could adopt, the following procedure would be used:

1) A radionuclide labeled, cell specific material is delivered to a patient, generally systemically, and the labeling material is allowed to circulate through the patients body until the material concentrates at intended target cells, resulting in radiolabeled (tagged) cells;
2) The target sites are generally located by techniques known to diagnosticians (palpation, nuclear scanning devices, cat scans, MRI, etc);
3) A probe incorporating features of the invention is placed in the vicinity of the tagged cells by known techniques such as those for delivery of catheters or endoscopes to desired locations or less invasive surgical techniques. Alternatively, the exposed tissue in an open surgical site can be scanned with the tip of the probe. X-ray or a CAT, MRI, or ultrasound scanner can also be used to guide the probe to the desired location. Because the probe which utilizes a gold collimator (one embodiment) will not interfere with, or its function be compromised by exposure to a magnetic field, the probe can be used in an operating theater where the patient as well as the surgeon are located within the field encompassed by the MRI unit.
4) As an added features, once tagged cells are located by the probe, as indicated by a visual or audible signal delivered by the electronic diagnostics attached to the proximal end of the probe, genetic material prepared for treatment purposes is delivered directly to the targeted/tagged cells using the probe to assure delivery to the vicinity of the targeted cells.

A further embodiment contemplated by the invention is the use of the above-described radio-detecting probe to map targeted tissue. In this embodiment the probe is mechanically, optically, electronically, or electromagnetically, connected to an x-y-z coordinate generating system which allows the position of the tip of the probe within the patient at the site of targeted tissue to be continuously identified and recorded and that position to be coordinated with the level of radiation emanating from a target located by the detector in the tip of the probe. As a result, the probe can be moved at a preset distance from target tissue, up and down as well as across the target tissue in multiple parallel paths to generate an image of the level of radioactive emissions from that tissue, showing portions thereof which have greater concentrations of the labeling compound.

The prior art, such as U.S. Pat. Nos. 5,042,486 and 5,899,860 to Pfeifer, et al. and U.S. Pat. No. 5,776,064 disclose the location of the catheter tip using a) a non-ionizing field, such as an electromagnetic or acoustic field, and/or receiving and transmitting antennas attached to the patient or b) a catheter mounted emitter with three receivers mounted on or surrounding the patient. FIG. 10 shows such transmitters 210 located in the probe tip. However, the invention contemplates the use of numerous other techniques to track and locate the probe tip, known to those skilled in the art.

Once the tip position is known, that position can be coordinated with the radiation reading there obtained, recorded and/or indicated by the photomultiplier diagnostic electronics 26. Also the inclusion of the position identifying transmitters 210 is not limited to the embodiment of FIG. 10 but can be incorporated in any of the other embodiments described and/or shown.

One skilled in the art will also recognize that the detector or scintillation crystal, while shown as a single detector, may in fact be multiple detectors, or an array of detectors, or a continuous film of detectors which are individually sensed or multiplexed. This provides the ability to generate an image of radioactive distributor across the radiation labeled target.

It is evident from the foregoing that there are many additional embodiments of the present invention which, while not expressly described herein, are within the scope of this invention and may suggest themselves to one of ordinary skill in the art. For example, the invention contemplates the use in place of the scintillation crystal, of multiple detectors, arrays of detectors, and continuous sheet of detector material capable of forming an image of radioactive concentration in targeted tissue. It is therefore intended that the invention be limited solely by the appended claims.

I claim:

1. A method of genetically altering diseased living tissue in a human body comprising:
   a) delivering a radionuclide labeled, tissue specific material to a patient,
   b) allowing the radionuclide labeled, tissue specific material to circulate through the patient's body until said material concentrates at intended diseased target tissue, resulting in radiolabeled diseased tissue,
   c) locating the situs of the radiolabeled diseased tissue,
   d) placing a nuclear probe having treatment delivery capabilities incorporated therewith adjacent the situs of the radio-labeled diseased tissue,
   e) targeting the radio-labeled diseased tissue using the nuclear probe, and
   f) delivering genetic material prepared for treatment purposes directly to the targeted radio-labeled diseased tissue while targeted by the probe to assure delivery of the genetic material to radiolabeled diseased tissue to be altered to modify the diseased tissue.

2. The method of claim 1 further comprising, between step b) and step c), placing the patient within the field of an MRI diagnostic device with the radio-labeled diseased tissue located within an area for diagnosis using the MRI device.

3. The method of claim 1 wherein the nuclear probe comprises multiple detectors, an array of detectors or a continuous film of detectors, said nuclear probe capable of providing an image of radiation distribution across the radiolabeled diseased tissue.

4. A method of altering diseased living tissue in a human body comprising:
   a) delivering a radionuclide labeled, tissue specific material to a patient,
   b) allowing the radionuclide labeled, tissue specific material to circulate through the patient's body until said material concentrates at intended diseased target tissue, resulting in radiolabeled diseased tissue,
   c) locating the situs of the radiolabeled diseased tissue,
   d) placing a nuclear probe having treatment delivery capabilities incorporated therewith adjacent the situs of the radio-labeled diseased tissue,
   e) targeting the radio-labeled diseased tissue using the nuclear probe, and
   f) delivering cells, biological vectors or carriers of genetic material prepared for treatment purposes directly to the targeted radio-labeled diseased tissue while targeted by the probe to assure delivery of the cells, biological vectors or carriers of genetic material to the radiolabeled diseased tissue to be altered to modify the diseased tissue.

5. The method of claim 4 further comprising, between step b) and step c), placing the patient within the field of an MRI diagnostic device with the radio-labeled diseased tissue located within an area for diagnosis using the MRI device.

6. The method of claim 4 wherein the nuclear probe comprises multiple detectors, and an array of detectors or a continuous film of detectors, said nuclear probe capable of providing an image of radiation distribution across the radiolabeled diseased tissue.

* * * * *